United States Patent [19]

Amer

[11] Patent Number: 4,540,285
[45] Date of Patent: Sep. 10, 1985

[54] PHOTOTHERMAL METHOD OF DETERMINING CALORIFIC PROPERTIES OF COAL

[75] Inventor: Nabil M. Amer, Berkeley, Calif.

[73] Assignee: The United States of America as represented by the United States Department of Energy, Washington, D.C.

[21] Appl. No.: 495,205

[22] Filed: May 16, 1983

[51] Int. Cl.³ ............................................. G01N 21/00
[52] U.S. Cl. ..................................................... 356/432
[58] Field of Search .......................................... 356/432

*Primary Examiner*—Bernard D. Pianalto
*Attorney, Agent, or Firm*—Harold M. Dixon; Roger S. Gaither; Judson R. Hightower

[57] ABSTRACT

Predetermined amounts of heat are generated within a coal sample (11) by directing pump light pulses (14) of predetermined energy content into a small surface region (16) of the sample (11). A beam (18) of probe light is directed along the sample surface (19) and deflection of the probe beam (18) from thermally induced changes of index of refraction in the fluid medium adjacent the heated region (16) are detected. Deflection amplitude and the phase lag of the deflection, relative to the initiating pump light pulse (14), are indicative of the calorific value and the porosity of the sample (11). The method provides rapid, accurate and non-destructive analysis of the heat producing capabilities of coal samples (11). In the preferred form, sequences of pump light pulses (14) of increasing durations are directed into the sample (11) at each of a series of minute regions (16) situated along a raster scan path (21) enabling detailed analysis of variations of thermal properties at different areas of the sample (11) and at different depths.

10 Claims, 2 Drawing Figures

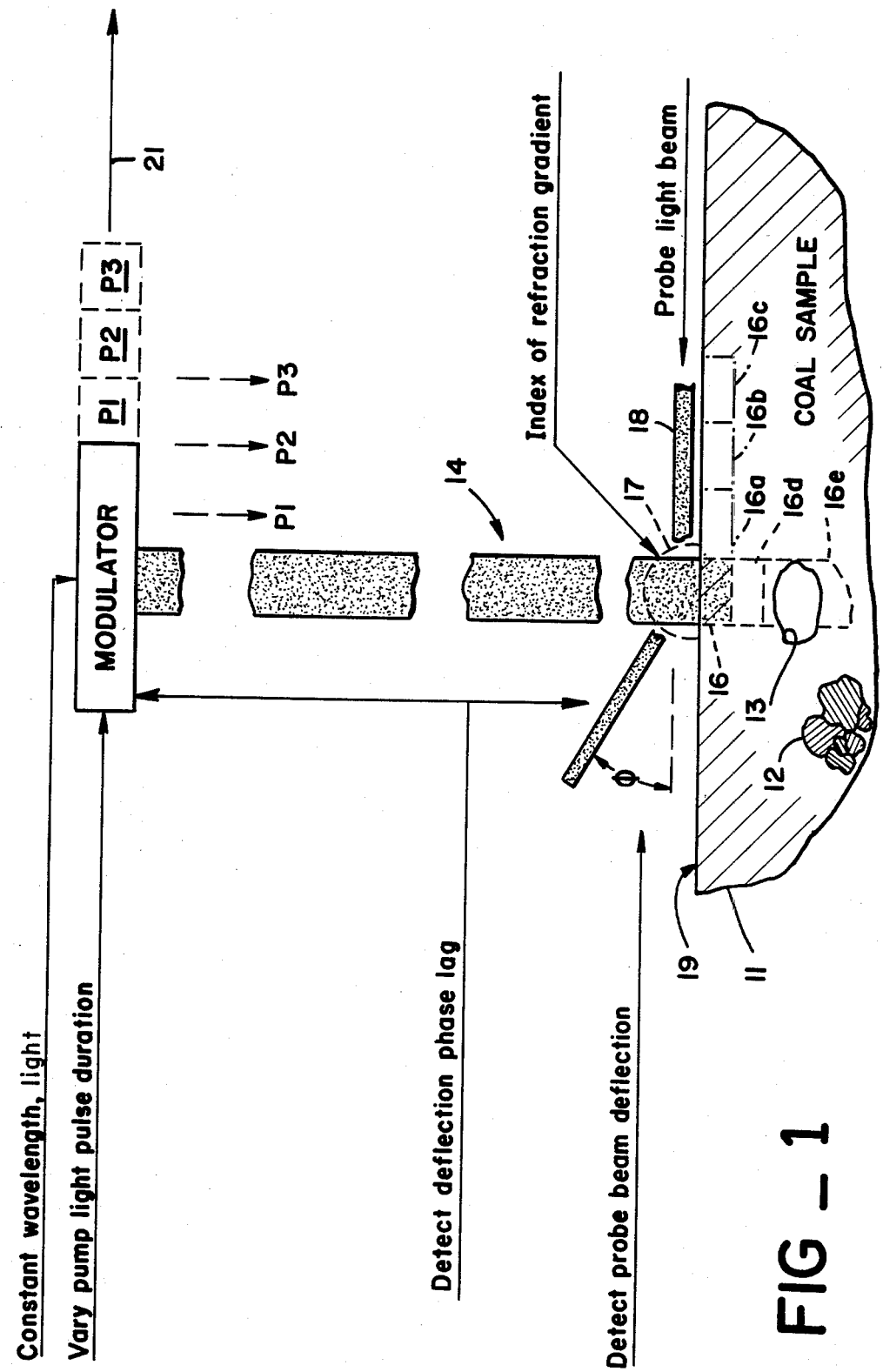
FIG—1

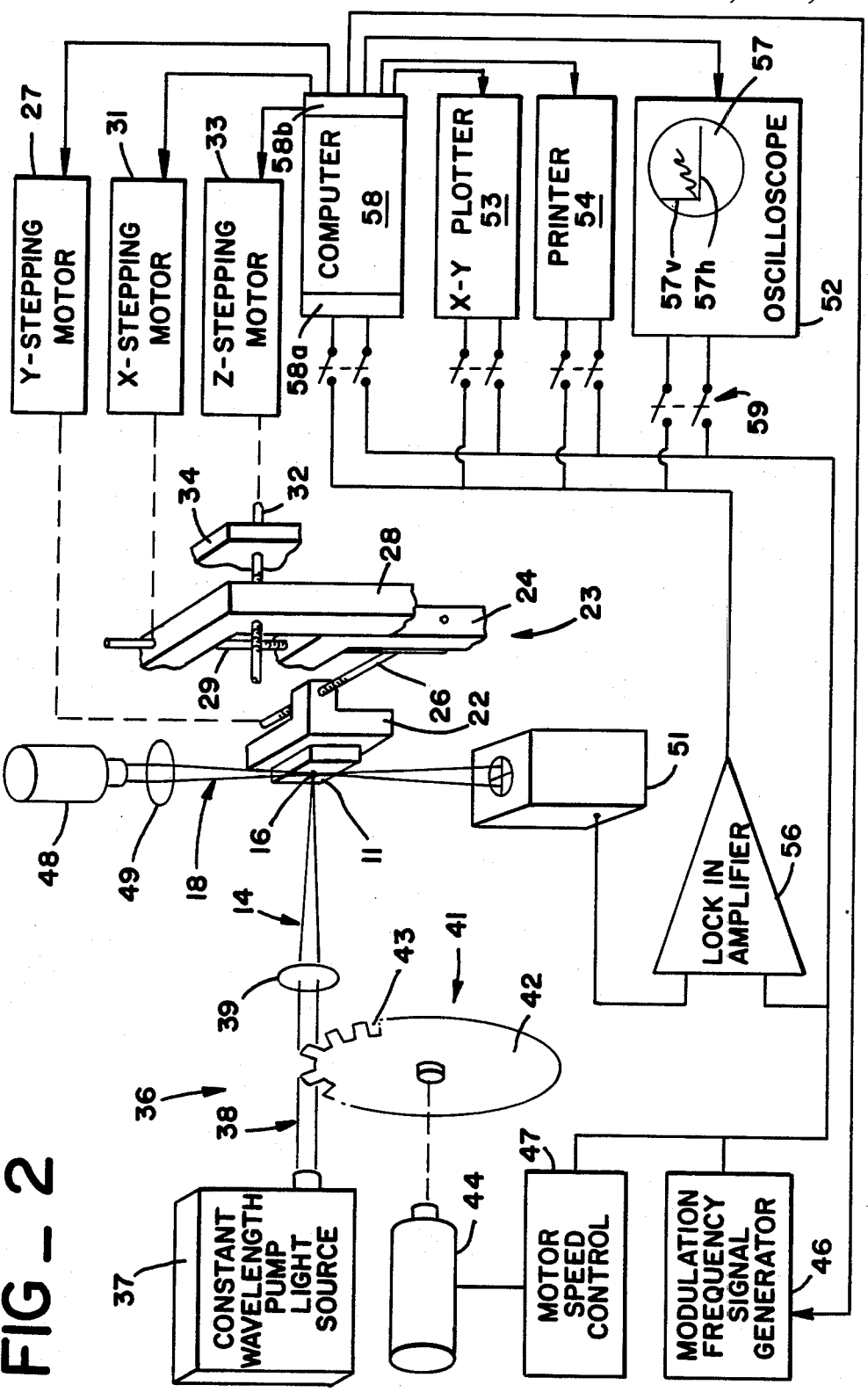
FIG_2

PHOTOTHERMAL METHOD OF DETERMINING CALORIFIC PROPERTIES OF COAL

The U.S. government has rights in this invention pursuant to contract number DE-AC03-76SFO0098 between the U.S. Department of Energy and the University of California.

BACKGROUND OF THE INVENTION

This invention relates to the analysis of thermal properties of coal and more particularly to a method of evaluating the porosities and heat producing capabilities of coal samples by utilizing non-destructive photothermal probing techniques.

Coal is a heterogeneous organic rock having a variable physical structure and chemical composition. Different samples may have different degrees of porosity. Macerals or microscopic inclusions of any of a number of distinct types may be present in varying proportions. Consequently the calorific value or heat producing capability of samples obtained from different mines or different locations in a particular mine may vary substantially. Evaluation of the calorific value or rank of particular samples can greatly facilitate mining, processing, marketing and utilization of coal.

Accurate testing of coal for calorific value by calorimetry or actual combustion of a sample or by quantitative chemical analysis requires time consuming operations under exactingly controlled conditions. A faster, non-destructive procedure would be much more efficient. Further, these conventional techniques do not provide information about variations of thermal properties at different regions of a given specimen unless such regions are separated to enable repetitive testings of a series of minute samples.

The thermal characteristics of coal are significantly affected by variations in porosity. Conventional calorimetry or chemical analysis both inherently correct for such variations but do not, in the absence of still further complications, provide any direct evaluation of the actual porosity of the sample. It would be highly useful in many instances to obtain an evaluation of porosity as such.

A generalized evaluation of the thermally significant properties of a coal sample may be adequate for many routine test purposes. In other cases, such as in technological research and development operations, it would be more useful to obtain a detailed knowledge of such properties including porosity between different small regions of a particular sample, preferably at the microscopic level and at different depths. Imaging of a sample in this manner, using known techniques, is extremely complicated.

SUMMARY OF THE INVENTION

It is a general object of this invention to facilitate analysis of the heat producing capabilities of coal samples.

It is a further object of the invention to provide a rapid, accurate, non-destructive method of determining calorific values of coal samples.

It is another object of the invention to provide for rapid, accurate, non-destructive evaluations of the porosity of coal samples.

It is still another object of the invention to enable detection of variations of thermally significant properties within coal samples at the microscopic level.

It is a further object of the invention to provide a non-destructive method of detecting the porosities and calorific values of sequences of minute specific regions within a coal sample including regions situated at a plurality of different depths within the sample.

Additional objects, advantages and novel features of the invention will be set forth in part in the description which follows, and in part will become apparent to those skilled in the art upon examination of the following or may be learned by practice of the invention.

The objects and advantages of the invention may be realized and attained by means of the instrumentalities and combinations particularly pointed out in the appended claims.

To achieve the foregoing and other objects and in accordance with the purposes of the present invention, as embodied and broadly described herein, an evaluation of the calorific value of a coal sample includes the steps of generating a predetermined quantity of heat within a predetermined surface region of the sample by directing light into the surface region, detecting the resulting heat transfer from the sample into the adjacent medium by detecting thermally induced changes of the index of refraction of the adjacent medium, and utilizing the changes of index of refraction as an indicator of the calorific value of the coal sample.

Preferably, in another aspect of the invention, the changes of the index of refraction are detected by directing a probe beam of light through the adjacent medium and measuring the deflection of the probe beam following the generation of heat within the surface region of the sample.

Preferably, in another aspect of the invention, the method includes the further steps of directing a sequence of pulses of light into the surface region of the sample, varying the duration of successive ones of the pulses to cause generation of different quantities of heat in response to successive pulses, and individually detecting the changes of index of refraction following successive pulses to evaluate the calorific value at a series of different depths within the sample.

Preferably, in another aspect of the invention, the method includes the further steps of sequentially directing the light to each of a series of different points on the sample which are located along a predetermined raster scan path, and detecting changes of index of refraction in the medium adjacent each of the points following the irradiation of each point with the light.

Preferably, in still another aspect of the invention, the light is modulated to irradiate the sample with light pulses of progressively changing duration, and includes the further step of detecting porosities in coal sample by detecting both the magnitude of the change of index of refraction and the phase lag of the change of index of refraction relative to the pulses of light.

The invention provides for rapid, accurate and convenient evaluation of thermally significant properties of coal, such as porosity and calorific value, without requiring combustion or chemical or physical breakdown of the sample. The invention further enables detection of variations in such properties at different areas and different depths within a sample and is capable of resolving such variations at the microscopic level when necessary.

BRIEF DESCRIPTION OF THE DRAWINGS

The accompanying drawings which are incorporated in and form a part of the specification, illustrate a preferred embodiment of the invention and, together with the description, serve to explain the principles of the invention. In the drawings:

FIG. 1 is a diagramatic illustration of operations performed on a coal sample, in accordance with one embodiment of the invention, in order to evaluate thermal properties including evaluating variations of such properties at different areas and at different depths within the sample, and FIG. 2 is a schematic depiction of apparatus suitable for performing an analysis of a coal sample in accordance with the method of FIG. 1.

DETAILED DESCRIPTION OF THE INVENTION

Reference will now be made to the present preferred embodiment of the invention, which is illustrated in the accompanying drawings.

Referring initially to FIG. 1 of the drawings, the morphological structure of a coal sample 11 typically exhibits a mixture of inclusions or macerals 12 of any of a variety of distinctly different types, such as vitrinite, exinite, micronite or fusinite among others. The macerals 12 are usually of varying size in a particular coal sample 11 and are present in varying proportions in samples obtained from different sites. A coal sample 11 also usually includes pores 13 of various sizes and the overall porosity of different samples may vary substantially.

Because of these variables, different lots of coal may have significantly different calorific values, the calorific value being a measure of the amount of heat which is produced by full combustion of a unit amount of the coal. As heat producing capability is a factor of primary importance in most usages of coal, it is often desirable that the calorific values of different specific batches be evaluated.

This is accomplished, in accordance with this embodiment of the invention, by steps which include directing pump light 14 of predetermined energy content into a surface region 16 of the sample 11. Optical absorption of such light 14 by the coal results in the generation of a predetermined amount of heat within the surface region 16. Such heat then diffuses away from region 16 of the sample in all directions provided that the sample is thick and extensive in relation to the penetration depth of the light into the coal. This results in heating of the volume of air or other gaseous or liquid medium 17 that is adjacent the heated region 16 of the coal. More particularly, a temporary thermal gradient occurs in the adjacent medium 17 and a temporary index of refraction gradient is present as the index of refraction of gases or liquids is a function of temperature.

The magnitude of the temporary thermal gradient in the adjacent medium 17 following a pulse of pump light 14 is dependent on the amount of heat energy generated in the coal sample 11 by the pulse and also on the calorific value of the coal in the heated region 16. The amount of generated heat energy can be predetermined since the opaque coal absorbs all energy in the pump light and converts it to heat and since the energy content of the pump light pulse itself can be predetermined by controlling the wavelength, intensity and duration of the pulse. Thus, as the amount of generated heat energy is known, the calorific value of the coal in the heated region 16 may be evaluated by measuring the temporary thermal gradient in the adjacent medium 17 or by measuring the associated index of refraction gradient in the medium.

The dependency of the thermal gradient in the adjacent medium 17 on the calorific value of the coal in heated region 16 may be understood by noting that heat transfer from region 16 to medium 17 is a function of the temperature at region 16. That temperature depends not only on the energy input from pump light pulse 14 but also on the specific heat value of the coal at region 16, specific heat being a measure of the amount of thermal energy needed to raise the temperature of a unit amount of a substance one degree. The specific heats of the various constituents of coal differ significantly. Thus the temperature rise produced at region 16 by a given energy input is dependent on the composition of the coal at that immediate region. Accordingly, the temperature and index of refraction gradients in the adjacent medium 17 are also dependent on the specific heat of the coal at region 16. As specific heat correlates closely with calorific value, the index of refraction gradient provides an indication of the calorific value of the coal at region 16. It should be noted that the relationship is an inverse one. In other words, a relatively high calorific value at region 16 results in relatively low thermal and index of refraction gradients in medium 17 and vice versa.

The method includes use of pump light 14 which is within the visible range or the ultra-violet range of the spectrum in order to avoid variations in the thermal and index of refraction gradients in medium 17 on account of possible variations in the chemical composition of the coal at region 16. Coal is uniformly and fully absorptive of wavelengths in the visible and ultra-violet ranges as evidenced by its blackness or total lack of coloration when illuminated by such wavelengths. This is not the case with respect to light in the infrared range where discriminatory absorption of specifc wavelengths occurs in a variable manner depending on differences in the chemical composition of the coal. The pump light 14 is also preferably of a single fixed wavelength or narrow range of fixed wavelengths so that the energy input to the sample 11 can be more readily determined.

In order to detect the index of refraction gradient changes in medium 17, a beam of probe light 18 is directed along the surface 19 of the coal sample 11 in transverse relationship to the path of pump light 14 and preferably as close to the surface as possible. The probe light beam 18 is directed through region 17 and is preferably a beam of fixed, single wavelength coherent light having a diameter smaller than that of the pump light beam 14. The deflection angle, $\phi$, of the probe beam 18 in passage through region 17 is detected, by means to be hereinafter described for example, in order to ascertain the index of refraction gradient which results from a pump light pulse 14.

The detected index of refraction gradient may be smaller than would otherwise be the case if one or more porosities 13 are present in the heated region 16 of the sample 11. Under that condition, the fixed amount of energy in the pump light pulse 14 diffuses more deeply into the sample 11 and consequently a lesser proportion of the heat is transferred to the adjacent medium at region 17. The reduced gradient can be recognized as being indicative of porosity rather than a higher calorific value at region 16 as it is accompanied by an increase in the time delay or phase lag of the peak gradient relative to the initiating pump light pulse 14. A longer time is required for diffusion of the more deeply generated heat to the surface 19 of the sample 11.

Accordingly the method, in its preferred form, includes the further step of detecting the phase lag of the probe beam 18 deflection relative to the initiating pump light pulse 14. The calorific value indicated by the peak probe beam 18 deflection may then be adjusted, if necessary, to correct for the effects of the porosity 13. Detection of the phase lag also enables a direct evaluation of the porosity of the sample 11 when that information is desired.

In some usages of the invention, a single sequence of the above desribed operations performed on a sizable region 16 of the sample 11 may provide sufficiently accurate and detailed information. Readings of calorific value and/or porosity made in that manner are essentially averaged values for the sizable region 16 and may be sufficiently indicative of the thermal properties of the sample as a whole. In other instances a more precise and detailed determination may be needed including data indicative of variations of calorific value and/or porosity between different regions of the sample 11. The method provides for obtaining such data, if necessary, with resolution at the microscopic level.

In particular, by utilizing single wavelength light sources and by utilizing lenses, the pump light 14 pulses and probe beam 18 may be focussed down to diameters of a few microns at the region 17 of intersection. The heat generation region 16 is then correspondingly minute and the probe beam deflection and phase data which is obtained is specific to that minute region of the sample 11. The origin of the pump light pulses 14 may then be sequentially shifted parallel to the sample surface 19, in steps, to successive positions P1, P2, P3 and the like along a scan path 21 with the above described operations being repeated at each step. Thus at each such position an evaluation of thermal properties is obtained for a different minute region 16a, 16b, 16c situated along the scan path 21. By scanning a sizable area of the sample 11 in this manner sufficiently detailed information is generated to provide for a constructed image depicting variations of thermal properties at a microscopic scale.

The method further provides for probing of the thermal properties at progressively greater depths within the sample 11. As the wavelength and intensity of the pump light is held constant, the energy content of an individual pump light pulse 14 is a function of the duration of the pulse. By progressively increasing the durations of successive pump light pulses 14a, 14b, 14c, the amount of heat generated in the sample 11 becomes progressively greater for each such pulse. The depth of the heated region 16 then becomes progressively greater with each such pulse as indicated at 16d and 16e in FIG. 1. Consequently probe beam 18 deflection readings and phase lag readings made concurrently with each such pump light pulse 14 are indicative of thermal properties at an increasingly greater depth in the sample 11 provided that such readings are adjusted to subtract the previously detected contributions from the preceding shallower heated regions 16. While the relatively high degree of opacity of coal limits the maximum penetration depth of pump light pulses 14 of practical intensities, the above described techniques enable subsurface probing of thermal properties to an extent that can provide highly useful information particularly where a three dimensional mapping of such properties on a microscopic scale is desired.

An example of apparatus suitable for practicing the above described operations is depicted in FIG. 2, other arrangements of components also being suitable for the purpose. In the system of FIG. 2 the coal sample 11 to be analyzed is temporarily secured to a specimen holder platform 22 which is controllably translatable in each of three mutually perpendicular directions. The translation means 23 may, for example, be similar to that employed in motor controlled microscope stages. Thus specimen holder 22 is slidable in a first or Y-axis direction relative to a first stage frame 24 in response to rotation of a first lead screw 26 which is driven by a Y-axis stepping motor 27. First frame 24 is in turn slidable in a perpendicular or X-axis direction relative to a second stage frame 28 in response to rotation of a second lead screw 29 turned by an X-axis stepping motor 31. The second frame 28 may be moved in the third or Z-axis direction by rotation of a third lead screw 32, driven by a Z-axis stepping motor 33, which is coupled to a stationary member 34 of the translation means.

Means 36 for directing pump light of predetermined energy content into the sample 11 includes a light source 37 of the form which emits a coherent beam 38 of light having a selected fixed wavelength and which in this example is a continuous wave dye laser. Non-coherent polychromatic light sources, such as a xenon arc lamp, may also be used in some instances if the output light is passed through optical bandpass filters to produce essentially monochromatic light containing only a narrow range of wavelengths.

Pump light from source 37 is directed to coal sample 11 through a focussing lens 39 which reduces the diameter of the light beam, at the surface of the sample, to define the previously described very small heated region 16. A modulator 41 cyclically interrupts the output light beam 38 from source 37 to produce the previously described sequences of light pulses 14 of progressively increasing duration.

Modulator 41 in this example is a beam chopper of the type having the rim of an opaque rotatable disc 42 situated in the path of the pump light 38. Notches 43 at the rim of the disc intermittantly transmit the pump light 38 to lens 39 and sample 11 as the disc is turned by a drive motor 44. Other forms of beam chopper known to the art may also be employed.

The timing and duration of the pump light pulses 14 are controlled with a modulation frequency signal generator 46 which produces a cyclical output voltage of adjustable frequency that controls the speed of the beam chopper drive motor 44 through motor control 47. Thus the duration of successive pump light pulses 14 may be progressively increased by progressively decreasing the output frequency of generator 46. In a typical analysis of a coal sample 11, the pump light pulse 14 frequency may be varied from about 2 KHz down to about 10 Hz while the pump light pulses are being directed to each heated region 16.

The probe beam 18 light in this example is produced by a He-Ne laser 48 which directs the probe light along the surface of coal sample 11 through another focussing lens 49 which reduces the diameter of the probe beam to less than that of pump light pulses 14 at the light beam intersection point adjacent the heated region 16 of the sample 11.

The focal point of lens 49 is located adjacent to the heated region 16 and thus the probe light beam 18 increases in diameter after passing the heated region and after being deflected by the index of refraction gradient adjacent the heated region as previously described. The degree of deflection is detected by a position sensor 51 positioned to receive the probe light beam after it has traveled past the sample. The position sensor 51 of this example is of the known quadrant form which produces electrical output pulses in response to displacement of a light beam from a predetermined position with the amplitude of the output pulses being a function of the degree of displacement.

The desired data on calorific value and on porosity is obtained by detecting the amplitudes of output pulses from position sensor 51 and by detecting the phase lag or timing of such pulses, relative to the initiating pulse 14 of pump light, by measuring the delay of the output pulses relative to the modulation frequency signals from generator 46. Such data may be obtained by transmiting the output pulses from sensor 51 and modulation signal generator 46 to any or all of a variety of data processing and display devices which in this example include an X-Y display or oscilloscope 52, an X-Y plotter 53 of the form which produces a graphical trace of signal values against a time base and a printer 54 of the type which digitizes and prints out the amplitudes and times of sets of incoming signals.

To enhance accuracy by suppressing spurious signals or circuit noise, output pulses from position sensor 51 are transmited to the devices 52, 53, 54 through one input of a lock-in amplifer or synchronous detector 56 of the known form which is sensitive only to signals having a frequency similar to or close to that of a control signal applied to another input which in the present case is the modulation frequency signal from generator 46.

If, for example, oscilloscope 52 is being utilized to obtain the desired data, the modulation frequency signal from generator 46 is used to provide the horizontal sweep frequency for the display at oscilloscope screen 57 and the output pulses from amplifier 56 are applied to the vertical sweep control. Horizontal and vertical scales, 57h and 57v respectively, may be provided on screen 57 to enable visual readout of the desired data. Oscilloscope 52 is of the known form having persistence controls so that a group of amplifier output pulses may be selected and temporarily retained on screen 57 for evaluation before proceeding on to display and evaluation of a subsequent group of pulses from the same sequence.

Calibration of the vertical scale 57v of oscilloscope 52 to enable visual readings of calorific values and calibration of the horizontal scale 57h to provide for evaluation of porosities from the phase lags of pulses may be accomplished by initially operating the system with samples of known calorific values and porosities.

Following readout of the data for one specific small region 16 of the coal sample 11, X-stepping motor 27 is operated to bring an adjacent small region into position to receive the pump light pulses 14 and the sequence of operations is repeated to obtain data for that region. After data has been obtained for regions 16 along an initial scan line, Y-stepping motor 27 is operated to enable similar operations along an adjacent parallel scan line and the process may be repeated to evaluate any desired area of the sample 11. Z-stepping motor 33 may be utilized to adjust for unevenness in the surface of the sample 11, if necessary.

While the several components of the system may be manually actuated and controlled, it is also possible to utilize a computer 58 to cycle the modulation frequency generator 46, stepping motors 27, 31, 33 and other components of the system if desired. Direct connection of amplifier 56 and modulation frequency signal generator 46 to the display devices 53, 54, 57 may be interrupted, for example with switches 59, and the output signals may be delivered to the computer 58 through an analog to digital converter 58a if the computer is of the digital form. The computer 58 may then transmit processed control signals to the above described components of the system through a digital to analog converter 58b if needed.

The foregoing description of a preferred embodiment of the invention has been presented for purposes of illustration and description. It is not intended to be exhaustive or to limit the invention to the precise form disclosed, and obviously many modifications and variations are possible in the light of the above teaching. The described embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

I claim:

1. In a method of evaluating the calorific value of a coal sample, the steps comprising:
   generating a predetermined quantity of heat within a predetermined surface region of said coal sample by directing light into said surface region,
   detecting the resulting heat transfer from said sample into the medium adjacent said region by detecting thermally induced changes of the index of refraction of said medium adjacent said region, and
   utilizing said changes of index of refraction as an indicator of said calorific value.

2. The method of claim 1 wherein said thermally induced changes of the index of refraction of said medium adjacent said region are detected by directing a probe beam of light through the volume of said medium which is adjacent said region and detecting the deflection of said probe beam at said volume of said medium following said generation of heat within said surface region of said sample.

3. The method of claim 1 including the further steps of:
   directing a sequence of pulses of said light into said region of said coal sample,
   varying the duration of successive ones of said pulses to cause generation of different predetermined quantities of heat in response to successive ones of said pulses, and
   individually detecting said changes of index of refraction following each of said successive pulses in order to evaluate said calorific value at a series of different depths within said sample.

4. The method of claim 3 including the step of modulating said light to cause said pulses of visible light of said sequence to be of progressively greater duration.

5. The method of claim 1 including the further steps of:
   sequentially directing said light to each of a series of different points on the surface of said sample which are located along a predetermined raster scan path thereon, and detecting said changes of index of refraction in the medium adjacent each of said points following irradiation thereof with said light.

6. The method of claim 1 wherein said light is modulated to irradiate said region of said sample with a sequence of pulses of light of progressively changing duration, and including the further step of:

detecting porosities within said coal sample by detecting both the magnitude of said change of index of refraction and the phase lag of said change of index of refraction relative to said pulses of light following each of said pulses of said sequence.

7. The method of claim 1 wherein said coal sample includes a plurality of different minerals, including the further step of utilizing light of a predetermined fixed wavelength spectrum that is substantially uniformly absorbed by each of said plurality of different minerals whereby the amount of said heat which is generated in said sample by said light is unaffected by variations in the mineral composition of said sample.

8. In a method of determining thermal characteristics of a coal sample, the steps comprising:

directing a pump beam of light of predetermined fixed wavelength into said sample at a predetermined area thereon to cause heating of said sample at said predetermined area and consequent heat transfer to a region of the fluid medium adjacent said area, modulating said pump beam of light into a sequence of light pulses of progressively increasing durations, directing a probe beam of coherent light of predetermined wavelength through said fluid medium region adjacent said area, detecting the amounts of deflection of said probe beam at said region following each of said light pulses, detecting the phase relationships of said deflections relative to said light pulses following each of said light pulses, and utilizing said detected deflections of said probe beam and said detected phase relationships as indicators of said thermal characteristics.

9. The method of claim 8 including the further steps of sequentially directing a plurality of said sequences of light pulses of progressively increasing durations into said sample at each of a plurality of predetermined areas thereon which are situated along a raster scan path on said sample, and detecting said deflections and phase relationships at each of said predetermined areas.

10. The method of claim 8 including the further step of varying the modulation frequency of said pump beam during said sequence of light pulses of progressively inceasing duration from about 2 KHz to about 10 Hz.

* * * * *